United States Patent [19]

Naylor

[11] 4,281,230
[45] Jul. 28, 1981

[54] ANTI-ARC PROD

[75] Inventor: Carl A. Naylor, York, Pa.

[73] Assignee: Allis-Chalmers Corporation, Milwaukee, Wis.

[21] Appl. No.: 81,937

[22] Filed: Oct. 4, 1979

[51] Int. Cl.³ .............................................. H01H 3/16
[52] U.S. Cl. .............................. 200/61.58 R; 29/879; 200/61.76; 200/61.85; 200/157; 324/51
[58] Field of Search ..................... 200/61.58 R, 61.76, 200/61.85, 157; 324/158 P, 51, 72.5; 339/31 T, 97 T, 108 TP; 29/878, 879, 880

[56] References Cited

U.S. PATENT DOCUMENTS

| 1,760,257 | 5/1930 | Smith | 200/157 UX |
|---|---|---|---|
| 2,234,834 | 3/1941 | Scott | 200/269 |
| 2,515,004 | 7/1950 | Haupt | 339/108 TP |
| 2,610,237 | 9/1952 | Benner | 324/51 X |
| 2,680,834 | 6/1954 | Burns et al. | 340/603 |
| 2,849,681 | 8/1958 | Belart | 324/72.5 X |

Primary Examiner—J. V. Truhe
Assistant Examiner—Morris Ginsburg
Attorney, Agent, or Firm—Robert C. Jones

[57] ABSTRACT

In a magnetic particle testing procedure, a spring loaded prod with contact points prevents arc strikes from occurring between the prod and a part under test. Positive pressure is applied to the prod which engages the contacts before current can flow to the part. Similarly, in removing the prod from the part with the prod power switch depressed, the arcing will occur in the prod assembly and not on the part under test.

6 Claims, 1 Drawing Figure

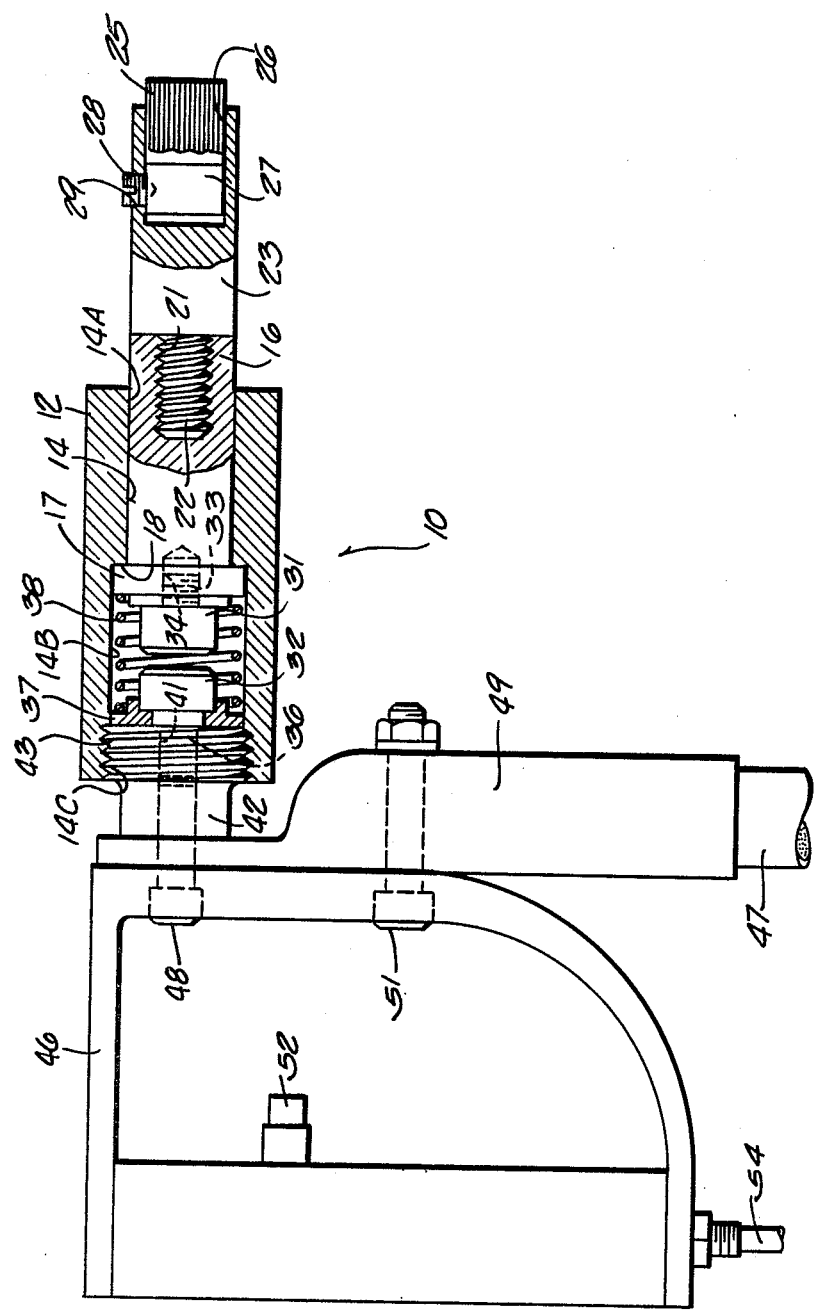

12

ANTI-ARC PROD

BACKGROUND OF THE INVENTION

The invention relates to an improvement in an apparatus for nondestructive testing of base metals, welds and localized repair areas utilizing dry magnetic particles.

In equipment fabricated for highly specialized requirements, it is essential that base metals, welds and localized repair areas be inspected for continuity of material to insure the integrity of the structure. In surface testing, prods are applied to the surface to be tested so that good electrical contact is made. However, with the use of manually held prods great care must be taken to obtain good electrical contact. This is true because poor electrical contact will result in arcing and possible burning of the finished machined surface as well as a reduction in the amount of current passed through the part being tested. In the past, the prods were positioned on the part under test while applying pressure to the prods. However, it is not uncommon to find that when the power switch is turned on the prods are not making good or firm contact with the part. As a result an arc strike occurs. Also, if a manually held prod is removed from the part under test before the power switch is released, an arc strike will occur. In either case the arc strike severally mars the surface of the part under test which will require repair and refinishing.

SUMMARY OF THE INVENTION

The spring loaded prod with contact points prevents arc strikes from occurring between the prod and the part under test. The prod must have a positive pressure applied which engages the contacts before the current can possibly flow into the part. Similarly, if the prod is removed from the part prematurely and the power switch is still depressed, the arcing will occur in the prod assembly—not on the part under test. To this purpose, so that arc strikes can be minimized from occurring between the prod and the item under test, a barrel of Micarda material houses a prod plunger which is constantly held under a biasing pressure by a spring. A set of normally open button contacts prevent the current from flowing through the assembly to the item under test unless pressure is applied to the braided wire tip. Once pressure is applied, the tip transfers the pressure to the extension which transfers pressure to the plunger which, in turn, closes the contacts. Consequently, the circuit is completed through a spacer to the connector and to the copper wire which is attached to the connector. The copper wire is connected to a power supply.

DESCRIPTION OF THE DRAWING

The single FIGURE is a view partly in section and partly in elevation of the anti-arc prod of the present invention.

DESCRIPTION OF THE INVENTION

As shown in the drawing, there is provided a novel improved anti-arc prod 10. The prod 10 includes a body member or barrel 12 fabricated of Micarda. A bore 14 of concentric sections 14A, 14B and 14C is formed in the barrel. The forward end or, as viewed in the drawing, the right end receives a prod plunger 16 slidable within the bore section 14A. To prevent the plunger 16 from sliding out of the right end of the barrel bore, the inner or left end of the plunger 16 is formed with a radial flange 17 which is adapted to abut the shoulder 18 by the bore section 14B.

The right or outer end of the plunger 16 is formed with a threaded axial blind bore 21 that is adapted to receive threaded stud portion 22 formed on the left end of a prod trip extension 23. A prod tip 25 fabricated in this particular example of ¾ inch braided copper wire is disposed within an axial blind bore 26 formed in the right end of the prod tip extension 23.

The end of the braided wire tip 25 which is disposed within the bore 26 of the tip extension 23 is brazed to effect a solidification of the braided wire. Around the brazed wires there is wrapped a copper band 27 which is welded around the brazed portion of the tip 25. A cone tipped set screw 28 is engaged in a threaded opening 29. The opening 29 is located in position to communicate with the bore 26 and provides access for the cone tip of the set screw 28 to enter into and firmly engage with the copper band welded around the inner end of the tip 25. This effectively locks the tip 25 to the extension but facilitates the replacement of the tip.

Rearwardly of the barrel 16 within the bore section 14B, there are provided a pair of spaced apart button contacts 31 and 32. The contact 31 is provided with a threaded stud 33 that is engaged in a threaded axial opening 34 formed in the inner or left end of the prod plunger 16. On the other hand, the contact button 32, having a threaded axial stud 36, extends through a suitable axial opening formed in a circular Micarda insulating spacer 37 that is disposed within the end of the bore section 14B. A spring 38 within the bore section 14B end acting between the spacer 37 and the inner end of the prod plunger 16 normally operates to maintain the contacts 31 and 32 apart. The Micarda insulating spacer 37 is utilized to insulate the spring and contact assembly such that current cannot flow through the spring and contact assembly in the normally "open" position. As previously mentioned, the threaded axial stud 36 of the contact 32 extends through a suitable axial opening in the spacer 37 and engages in a threaded axial bore 41 formed in a spacer 42.

The spacer 42 is provided with an enlarged threaded head portion 43 which is engaged in the threaded bore section 14C of the prod barrel 12. The axial end face of the spacer head portion 43 abuts the axial end face of the contact spacer 37 thereby locking the spacer 37 between the contact button 32 and the head 43 of the spacer 42.

With the structure thus far described, it can be seen that an energizing engagement of the contact buttons 31 and 32 will occur only when sufficient force is exerted on the tip 25. This, of course, will only occur when the prod 10 is fully and properly engaged with the workpiece to be tested.

Manipulation and the supply of energy to the anti-arc prod is effected through a handle 46 and a power line cable 47. The electrical supply cable 47 is electrically connected to the anti-arc prod through the shank of the spacer 42. As shown, the cable 47 is secured to the spacer via a bolt 48 which extends through the D-configured handle 46 and a cable connector 49 into threaded engagement into the bore 41 formed in the spacer 42. Another bolt 51 is provided to prevent swivel movement of the cable relative to the handle. Within the handle 46 is a power switch 52 of the contact type connected via a conductor 54 to energize a transformer (not shown) by completing an open circuit via the two wires of the cable conductor 54 to supply current to the prod tip 25. The power switch 52 is carried in a Micarda insulating portion of the D-shaped handle 46 and is here required to engage a power transformer (not shown) which is remotely located. The power transformer effects energization of the two wire power cable 47.

In operation, the braided prod tip 25 is placed upon the surface to be tested. The operator then applies sufficient pressure to the prod handle 46 so that the force is transferred to close the button contacts 31 and 32 against the counteracting force of the spring 38. The power switch 52 is then activated to supply current to the prod tip 25 for the magnetic particle testing, which is a nondestructive testing means for detecting discontinuities in ferromagnetic materials. In this test, dry particles of iron or magnetic iron oxide are applied to the surface or localized area of the ferromagnetic material specimen and the specimen is magnetized. The pattern formed by the particles indicates surface or near-surface discontinuities such as fatigue cracks, etc. After the test has been completed, the power switch 52 is released and the prod removed from the part under test. Should it occur, as it often does, that the release of the power switch 52 and removal of the prod tip 25 from the part under test is not coordinated, an arc strike occurs between the tip and the surface of the test part. However, with the present invention, removal of pressure from the prod will allow the spring 38 to operate moving the contact buttons 31 and 32 apart. Thus, the arc strike will occur between the button contacts within the prod assembly. Similarly, should it occur that the power switch 52 is activated before good contact is made between the prod tip 25 and the surface of the part under test, the arc strike will also occur between the contact buttons.

It is apparent from the foregoing description of the novel anti-arc prod that a unique and simplified structure has been provided and one that is extremely successful in minimizing arc strikes during magnetic particle testing. It will also be appreciated that under test operations a pair of the anti-arc prods will be utilized.

The embodiments of the invention in which an exclusive property or privilege is claimed are defined as follows:

1. An anti-arc prod for magnetic particle testing of a surface of a part;
   a handle;
   a body member having an axial opening carried by said handle;
   a movable member slidably carried within the axial opening of said body member;
   a prod tip removably secured to said movable member for axial movement relative to said body member;
   a pair of normally open contact means within the axial opening of said body member; said normally open contact means being movable to a closed position upon pressure engagement of said prod tip with the surface of a part to be tested;
   yieldable means operating between said contact means carried within the axial opening of said body member and normally operating to maintain said contact means in their normally open position;
   current carrying means for connection between a current source of high amperage/low voltage electricity and one of said contact means, and;
   a power switch carried by said handle and operable when actuated to effect the flow of current from a source of high amperage/low voltage electricity through said contact means to said prod tip.

2. An anti-arc prod according to claim 1 wherein said contact means include first and second button contacts, the first of said button contacts being secured to the inner end of said movable member within the axial opening of said body member for movement therewith, the second of said contact buttons being removably fixed within the axial opening of said body member in spaced apart relationship with respect to the first contact button that is associated with said movable member.

3. An anti-arc prod according to claim 2 wherein said movable member is provided with an axial opening in the end thereof which extends outwardly of the axial opening in said body member; and,
   said prod tip is constructed of braided copper wire having one end portion brazed to solidify the braided wire, said brazed end of said prod tip being disposed within the opening in the outer end of said movable member; and,
   means carried by said movable member in position to engage with the brazed end of said prod tip within the opening in said movable member to releaseably lock said prod tip to said movable member.

4. An anti-arc prod according to claim 3 wherein there is provided metallic securing means removably connected to said prod handle and to said body member and operable to secure them together as a unit; and,
   said current carrying means being electrically connected to said securing means.

5. An anti-arc prod according to claim 4 wherein said metallic securing means is provided with a threaded end portion which is threadedly engaged in a threaded section formed in the end of said body member, and said second contact button is removably secured to the axial inner end face of said securing means within the opening of said body member.

6. An anti-arc prod according to claim 5 wherein said body member is constructed of an electrical insulating material such as Micarda; and,
   means of an electrical insulating material such as Micarda constructed and arranged to insulate said yieldable means and said contact buttons in a manner that current cannot flow through said yieldable means and said contact buttons when said contacts are in their normally open position.

* * * * *